US010639117B2

(12) United States Patent
Johnson et al.

(10) Patent No.: US 10,639,117 B2
(45) Date of Patent: *May 5, 2020

(54) TACTILE FEEDBACK SYSTEM FOR ROBOTIC SURGERY

(71) Applicant: University of Pittsburgh—Of the Commonwealth System of Higher Education, Pittsburgh, PA (US)

(72) Inventors: Paul J. Johnson, Pittsburgh, PA (US); Umamaheswar Duvvuri, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 469 days.

This patent is subject to a terminal disclaimer.

(21) Appl. No.: 15/415,501

(22) Filed: Jan. 25, 2017

(65) Prior Publication Data

US 2017/0128148 A1 May 11, 2017

Related U.S. Application Data

(63) Continuation of application No. 13/605,098, filed on Sep. 6, 2012, now Pat. No. 9,592,093.
(Continued)

(51) Int. Cl.
*H05K 7/00* (2006.01)
*A61B 34/00* (2016.01)
(Continued)

(52) U.S. Cl.
CPC .............. *A61B 34/76* (2016.02); *A61B 17/29* (2013.01); *A61B 34/20* (2016.02); *A61B 90/10* (2016.02);
(Continued)

(58) Field of Classification Search
CPC ......... A61B 19/20; A61B 90/10; A61B 34/76; A61B 17/29; A61B 2090/065; H05K 7/00; Y10S 901/46
(Continued)

(56) References Cited

U.S. PATENT DOCUMENTS 6,313,514 B1 * 11/2001 Winterer ................. B81B 7/007
257/417
6,445,284 B1 * 9/2002 Cruz-Hernandez ..... G06F 3/016
340/4.12
(Continued)

OTHER PUBLICATIONS

Dargahi et al., "An Endoscopic Force-position Sensor Grasper with Minimum Sensors", Can. J. Elect. Comput. Eng., vol. 28, No. 3/4, Jul./Oct. 2003, 7 pgs.
(Continued)

*Primary Examiner* — Vy Q Bui
(74) *Attorney, Agent, or Firm* — Klarquist Sparkman, LLP

(57) ABSTRACT

Apparatuses and methods for the haptic sensation of forces at a remote location. Groups of MEMS-based pressure sensors are combined into sensor arrays. In some embodiments, the pressure sensors are encased in silicone or other elastomeric substance to allow for routine use in the aqueous environment of the body. The sensor arrays may be housed in a bio-compatible material (e.g., stainless steel, plastic) and may be attached to a printed circuit board to allow the electrical signal generated by the sensors to be communicated to a user. The sensor arrays may be used with faceplates that directly interact with the target tissue or object. The faceplates may be rough, smooth, serrated, or any other texture. The present apparatuses and methods are particularly well suited for robotic surgery and may be used wherever haptic sensing of forces at a remote location is desired.

22 Claims, 9 Drawing Sheets

Related U.S. Application Data

(60) Provisional application No. 61/531,266, filed on Sep. 6, 2011.

(51) Int. Cl.
| | |
|---|---|
| *A61B 17/29* | (2006.01) |
| *A61B 90/10* | (2016.01) |
| *A61B 34/20* | (2016.01) |
| *A61B 17/28* | (2006.01) |
| *A61B 90/00* | (2016.01) |

(52) U.S. Cl.
CPC ........ H05K 7/00 (2013.01); *A61B 2017/2825* (2013.01); *A61B 2090/065* (2016.02); *Y10S 901/46* (2013.01)

(58) Field of Classification Search
USPC .. 606/1, 37, 42, 51, 52, 130, 170, 205, 207, 606/208; 227/176.1, 178.1, 180.1
See application file for complete search history.

(56) References Cited

U.S. PATENT DOCUMENTS

| | | | | |
|---|---|---|---|---|
| 6,931,938 | B2 * | 8/2005 | Knirck | G01L 1/205 73/753 |
| 8,945,174 | B2 | 2/2015 | Blumenkranz | |
| 8,992,422 | B2 * | 3/2015 | Spivey | A61B 17/07207 600/153 |
| 2007/0078484 | A1 * | 4/2007 | Talarico | A61B 17/29 606/205 |

OTHER PUBLICATIONS

Dargahi et al., "Theoretical and Experimental Analysis of a Piezo-electric Tactile Sensor for Use in Endoscopic Surgery", *Sensor Review*, vol. 24, No. 1, 2004, 10 pgs.

Heo et al., "Tactile Sensor Arrays Using Fiber Bragg Grating Sensors", *Sensors and Actuators A*, vol. 26, 2006, 16 pgs.

King et al., "A Multielement Tactile Feedback System for Robot-Assisted Minimally Invasive Surgery", *IEEE Transactions on Haptics*, vol. 2, No. 1, 2009, 5 pgs.

Rosen et al., "Force Controlled and Teleoperated Endoscopic Grasper for Minimally Invasive Surgery-Experimental Performance Evaluation", IEEE, *Transactions on Biomedical Engineering*, vol. 46, No. 10, Oct. 1999, 10 pgs.

Sezen et al., "Novel MEMS Stiffness Sensor for Force and Elasticity Measurements", *Sensors and Actuators A*, vol. 158, 2010, 8 pgs.

Office Action from the United States Patent & Trademark Office in co-pending U.S. Appl. No. 13/605,098, dated Oct. 6, 2015, 7 pages.

Office Action from the United States Patent & Trademark Office in co-pending U.S. Appl. No. 13/605,098, dated Apr. 20, 2016, 8 pages.

Notice of Allowance from the United States Patent & Trademark Office in co-pending U.S. Appl. No. 13/605,098, dated Oct. 26, 2016, 7 pages.

* cited by examiner

100

104
112
108
116

TACTILE FEEDBACK SYSTEM FOR ROBOTIC SURGERY

CROSS REFERENCE TO RELATED APPLICATION

This is a continuation of U.S. patent application Ser. No. 13/605,098, filed Sep. 6, 2012, which claims the benefit of U.S. Provisional Patent Application No. 61/531,266, filed Sep. 6, 2011, both of which are hereby incorporated by reference.

FIELD

The present disclosure relates generally to the field of surgery and specifically to methods and systems for robotic and laparoscopic surgery providing improved tactile sensation to the surgeon.

BACKGROUND

Surgical robots with complex maneuvering capabilities are able to perform surgery by entering the body through tiny incisions. This less invasive approach results in decreased blood loss, significantly reduced recovery time, and lower overall healthcare costs when compared with traditional open surgery. For these reasons, robotic surgical systems are becoming a valuable asset to most major surgical centers. However, the use of surgical robots is currently limited to a small number of simple procedures because of one constraint: the design of current surgical robotic tools fails to provide the surgeon with an adequate sense of the forces being exerted on the tissue by the surgical instruments. This sensory input, termed tactile perception, is vitally important to medical professionals during surgical manipulation of tissue.

In traditional surgery, surgeons use the tactile perception of their fingertips to ascertain how hard to pull and grasp tissue without causing unwanted damage. Surgeons also use their tactile perception to assess the stiffness, density or texture of different tissues to determine what type of tissue it is. In minimally invasive robotic surgery, this tactile perception is lost and surgeons are left "blind" as to touch. This lack of haptic sensation poses the risk of unnecessary tissue damage and loss of valuable tactile information, and in many surgeries this risk outweighs the benefits that accompany robotic surgery. Thus; robotic surgery is excluded from use in many surgical procedures where it would prove extremely useful.

Ideally, a surgical tool for use in minimally invasive surgery would satisfy several criteria. Such a tool may include sensors capable of providing accurate and physiologically relevant information to the surgeon at appropriate spatial resolution. Sensors should be able to provide accurate measurements within the large range of pressures experienced at the tip of the graspers which range from very low levels up to pressures of 900 kPa. Further, the tool would possess a tissue-tool interface that allows appropriate grasping and manipulation of tissues and a profile that does not damage surrounding, non-target tissue.

Many research groups have attempted the design of surgical instruments that provide improved force and tactile perception to the surgeon; however, these efforts have not generated an appropriate tool for surgical use. One group attached strain gauges on the grasper jaws that bend with the grasper jaws and output a voltage signal corresponding to the amount of force exerted. Dargahi J., Najarian S. "An endoscopic force position grasper and minimum sensors," *Canadian Journal of Electrical and Computer Engineering*, (2004) 28: 151-166. The design disclosed therein is able to determine the magnitude and location of a force within the jaws but does not provide force distribution maps that may be beneficial to a user.

Rosen et al. disclosed design of a remote control handle coupled to a pair of graspers. Rosen, J., Hannaford, B., MacFarlane, M., and Sinanan, M., "Force controlled and teleoperated endoscopic grasper for minimally invasive surgery—Experimental performance evaluation." *IEEE Transactions on Biomedical Engineering*, (1999) 46: 1212-1221. Using optical encoders and actuators, the apparatus relays forces exerted at the instrument's jaws to the teleoperated unit. This design can potentially provide valuable information about local tissue compliance but utilizes only one bulk measurement that lacks adequate spatial resolution, potentially causing the surgeon to generalize inappropriately to a large tissue region.

Other groups have used microelectromechanical systems (MEMS) technology to develop sensor arrays to provide pressure distribution maps. Dargahi J., Najarian S. "Theorhetical and experimental analysis of a piezoelectric tactile sensor for use in endoscopic surgery" *Sensor Review*, (2004) 24:74-83; Heo J., Chung J., Lee J., "Tactile sensor arrays using fiber Bragg grating sensors" *Sensors and Actuators A: Physical*, (2006) 126:312-327; Peng P., Sezen A., Rajamani R., Erdman A. "Novel MEMS stiffness sensor for force and elasticity measurements" *Sensors and Actuators A*, (2010) 158:10-17. However, these designs have limited utility due to a lack of functional integration into endoscopic tools (i.e., they are unable to adequately manipulate tissue), inadequate resolution due to the size of the force transducers, and/or possess low upper limits of pressure ranges that are inappropriate for surgical application.

King et al. reported on an innovative design to be used with the Da Vinci robot which provides a low-resolution force distribution via an array of piezoresistive force sensors. King C., Culjat M., Franco M., Bisley, J., Cannan G., Dutson E., Gnmdfest V., "A multielement tactile feedback system for robot-assisted minimally invasive surgery" *IEEE Transactions on Haptics*, (2009) 2:52-56. Information from these sensors is then transmitted to 2×3 tactile display placed on the Da Vinci control unit at the surgeon's fingertips. The limitations of this design are spatial resolution and certain inaccuracies associated with the use of piezoresistive force sensors. Their system also lacked a functional grasping surface.

Thus, there remains a longstanding, unresolved need in the medical community for surgical tools used in minimally invasive surgery that have an effective dynamic range of force measurement and sufficient spatial resolution to selectively and effectively manipulate the target tissue, while at the same time minimizing damage to surrounding non-target tissue. Further, the profile of such surgical tools should be such that it has minimal impact on the tissue through which it passes en route to the target tissue. The present disclosure addresses these needs.

SUMMARY

The present disclosure provides a novel system capable of providing a user with accurate information about the magnitude and spatial distribution of forces at the interface between a surgical tool and a target tissue. The present disclosure further allows those forces to be sensed by the user through an interface that allows the surgical tool to be used during minimally invasive surgery. The present disclosure may include two main components: (1) A set of surgical instruments having pressure sensors at strategic locations within the tool, and (2) a user interface and control system that employs electromechanical actuation to "push back" at the user's fingertips to allow remote sensation of pressure being applied to the tissue by the surgical tool Additionally, the profile of the presently claimed surgical devices provides for minimal damage to the tissue through which the surgical tools must pass en route to the target tissue.

The apparatuses, systems, and methods of the present disclosure may employ sensor arrays for sensing forces at a surface, comprising a plurality of pressure sensors, wherein said plurality of pressure sensors are arranged in an array, wherein said pressure sensors are surrounded by an elastomeric substance; a printed circuit board, wherein said pressure sensors are operably connected to said printed circuit board; and a housing, wherein said housing includes said plurality of pressure sensors, said elastomeric substance, and said printed circuit board. The pressure sensors may be microelectromechanical system-based pressure sensors. The elastomeric substance is preferably corrosive-resistant and may be silicone, non-reactive gel, or non-reactive fluid. The sensors may be placed in a housing that is fabricated from a non-corrosive substance such as metal or plastic. In some embodiments, the pressure sensors possess a linear response to force. When using a surgical tool, the sensor arrays of the present disclosure may include a faceplate that may be smooth, textured or serrated, depending on the application in which the present disclosure is employed.

BRIEF DESCRIPTION OF THE DRAWINGS

For the present disclosure to be clearly understood and readily practiced, the present disclosure will be described in conjunction with the following figures, wherein like reference characters designate the same or similar elements, which figures are incorporated into and constitute a part of the specification, wherein.

DETAILED DESCRIPTION

It is to be understood that the figures and descriptions of the present disclosure have been simplified to illustrate elements that are relevant for a clear understanding of the disclosure, while eliminating for purposes of clarity, other elements that may be well known.

The systems and methods of the present disclosure provide surgeons with an accurate and sensitive perception of the tissue that is being manipulated during robotic or laparoscopic surgery. The present disclosure employs sensors that allow for an improved spatial resolution and responsiveness over a broad range of relevant pressures when compared to prior art surgical tools.

The surgical instrument embodiments of the present disclosure preferably include a plurality of micro-pressure sensors located within the base of jaws used to manipulate tissue. In some embodiments, the micro-pressure sensors are MEMS-based sensors. When chosen appropriately, the MEMS sensor arrays are capable of providing a linear response to force stimuli over the relevant physiological range. A representative micro-pressure sensor is the cubic micro-pressure sensor part number SM5108 obtainable from Silicon Microstructures. In some embodiments, the individual MEMS sensors are cubic and may be seemed to the circuit board. The micro-pressure sensors may also implemented by imprinting on a thin circuit board. The sensors may be coated with a protective silicone elastomer layer to allow the surgical tool to operate in the water-based environment of the body. For embodiments where the sensor arrays of the present disclosure are used in other types of corrosive environments, the protective elastomeric layer may be formed from a substance from that is resistant to whatever corrosive substances are in the environment.

In some embodiments, the sensor element size resolution is approximately 1.6 mm×1.7 mm, though this resolution may be altered by changing the size of the sensors with resolutions of approximately 0.65 mm×0.65 mm achievable. While the present disclosure is described in the context of a grasping embodiment, the disclosure is not so limited. The sensor arrays of the present disclosure may be used in graspers, forceps, scissors, trocars, and instrument shafts (to monitor lateral displacement of instruments against patient anatomy) within the context of the present disclosure. The limited circuitry used in implementing the sensing systems of the present disclosure allows the housing of the surgical tool in which they are placed to be relatively small compared to prior art surgical tools. The physical profile of the devices employing the sensing arrays of the present disclosure are thus reduced in size compared to prior art apparatuses and provide a concomitant reduction in ancillary tissue damage during surgery.

Figure 1A:
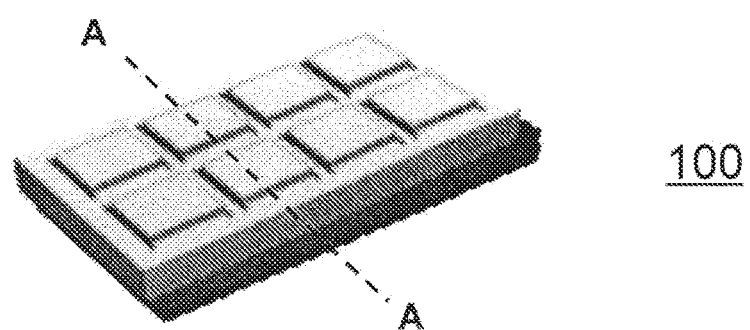
FIGS. 1A-1B provides a profile and cross-sectional view of a sensor array of the present disclosure.

One embodiment of the sensing arrays of the present disclosure is shown in FIG. 1A. The sensing array displayed has a 2×4 sensor array 100. The number and geometry of sensors may be varied to provide for appropriate sensory assessment of the surgical site. Broad ranges of both number and geometry of sensors are contemplated within the scope of the present disclosure.

Figure 1B:
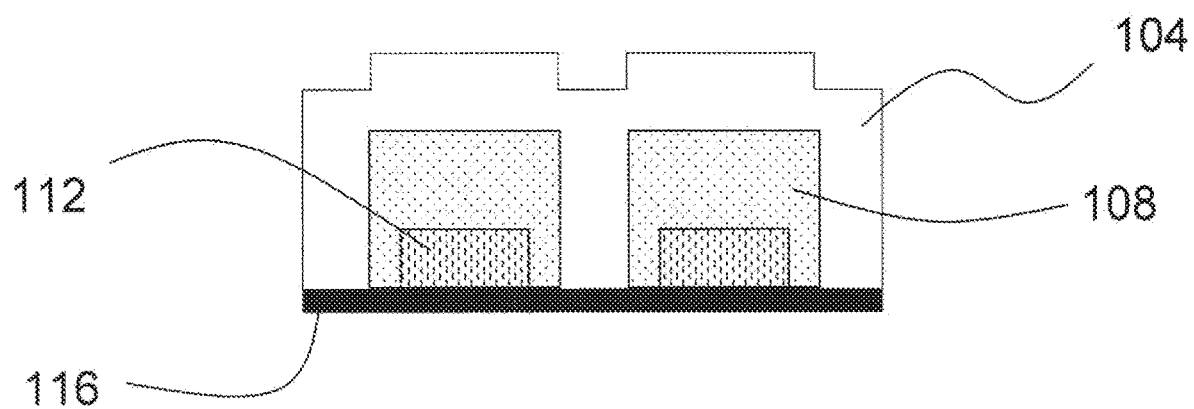

A cross-section of sensor array 100 is shown in FIG. 1B. In this embodiment, the micro-pressure sensor is a MEMS sensor die 112. The sensor die 112 is attached to a printed circuit board 116 at the base of the sensor array 100. To preserve the integrity of the sensor dice during surgery, they are coated in silicone 108, though other non-reactive elastomers, gels, or fluids may be used to surround the sensor 112. The silicone 108 in this embodiment is in turn surrounded by a plastic housing 104 in the shape of a grid as shown in FIG. 1A. The plastic housing provides structure to the sensing array and allows it to be manipulated routinely by medical professionals.

Figure 2:
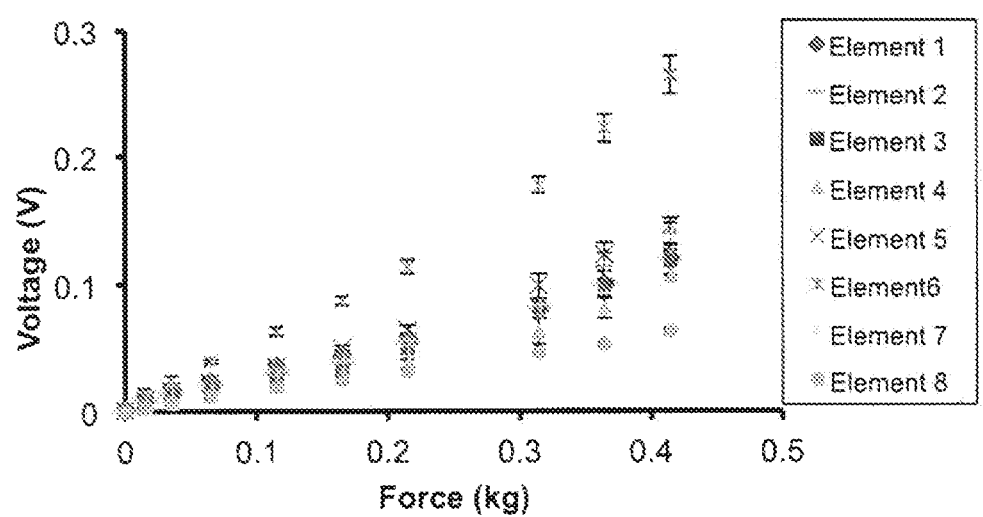
FIG. 2 displays the response profile of the sensors of the present disclosure.

A sensing array that is appropriate for surgical use should have both a linear response to force and the ability to acutely discern and isolate force input to the array. To assess the response profile of typical sensing arrays of the present disclosure, a set of experiments were run in which a load was applied to the top of each element within the array. Specifically, a mounted linear bearing was used to deliver a range of forces to an individual pad of the sensor array of FIG. 1 such that eight elements were tested. Each sensor element was characterized by measuring voltage output from each sensor die as the load was applied to the top of the element. As shown in FIG. 2, each sensor was found to have a linear response up to 400 grams. The use of deformable silicone raises the question of hysteresis, but the present sensory array design displays minimal hysteresis effects while providing a reproducible response to the load (error bars are standard deviation, N=5).

The data are summarized in the table below.

|  | Hysteresis (%) | | Sensitivity | Linear |
| --- | --- | --- | --- | --- |
|  | Average | Std. Dev. | (Mv/V/g) | Regression |
| Element 1 | 1.25% | 0.71% | 0.0346 | 0.988 |
| Element 2 | 1.44% | 0.84% | 0.0352 | 0.990 |
| Element 3 | 1.62% | 0.43% | 0.0359 | 0.988 |
| Element 4 | 0.00% | 0.46% | 0.0314 | 0.983 |
| Element 5 | 1.04% | 1.07% | 0.0443 | 0.966 |
| Element 6 | −0.32% | 1.14% | 0.0807 | 0.991 |
| Element 7 | 1.49% | 1.37% | 0.0421 | 0.990 |
| Element 8 | 4.31% | 1.87% | 0.200 | 0.990 |

Figure 3:
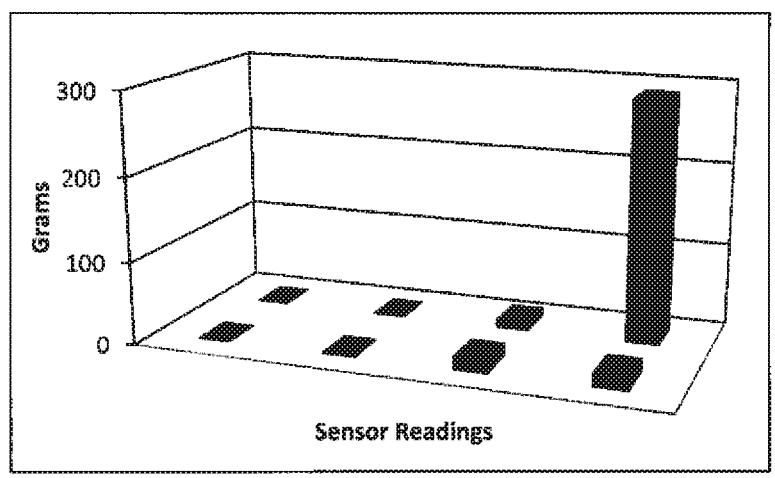
FIG. 3 shows the spatial sensitivity of the sensor arrays of the present disclosure.
Figure 3:
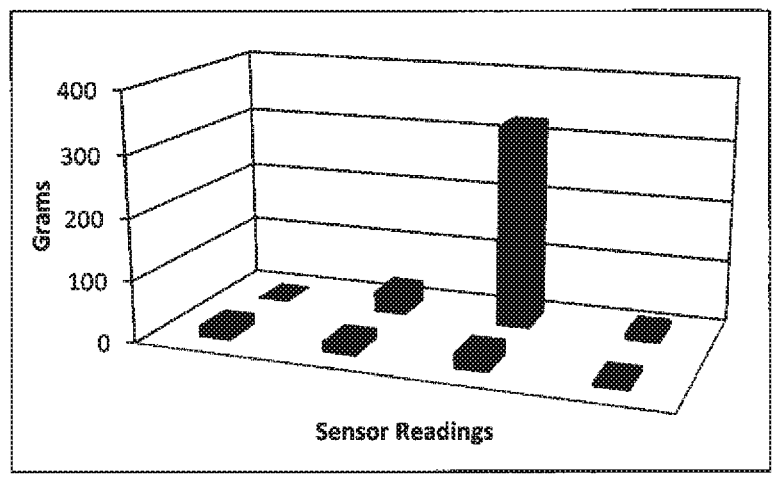

To assess whether the present sensor array was capable of discerning force stimulation of a single element, a separate test was performed. Force was applied to a single element of the sensor array and the force measured by all sensors was assessed. FIG. 3 shows the results of two such experiments in which two different elements were sequentially tested. As is clear from the figure, the sensor arrays of the present disclosure display minimal cross-talk such that the force output of individual sensors accurately represent the forces sensed at that specific point on the sensor array.

Figure 4A:
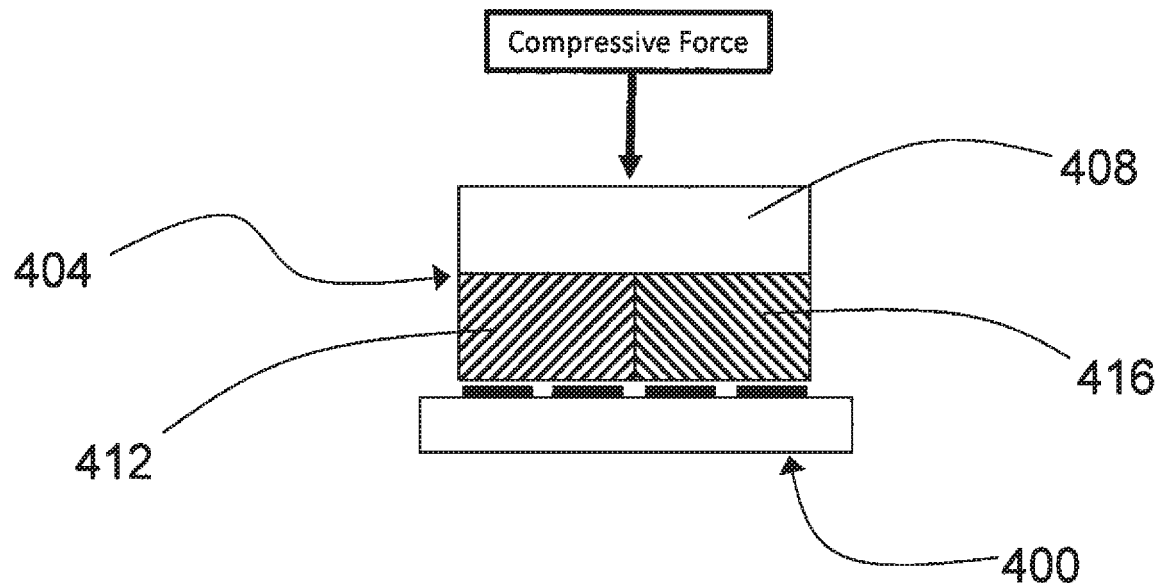
FIGS. 4A-4C demonstrates the limited crosstalk of the sensor arrays of the present disclosure.
Figure 4B:
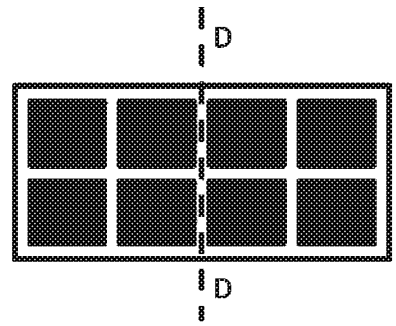
Figure 4C:
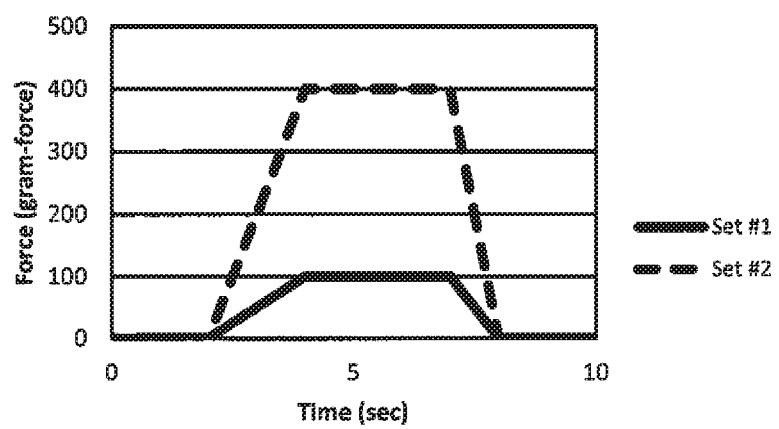

Finally, the ability of the sensor arrays of the present disclosure to discern a varied force stimulus was assessed. A synthetic tissue pad 404 was constructed in which two materials were employed to stimulate a 2×4 sensor array 400 of the present disclosure as shown in FIG. 4A. On the top of the pad, a firm material 408 was placed to allow force to be distributed to the materials below. The lower portion of the pad included two distinct synthetic materials that differed in compliance, i.e., firmness or deformability. As shown in FIG. 4A, the portion on the left 412 is a less compliant silicone material and the portion on the right 416 is more compliant synthetic fat material. The three mm-thick tissue pad 404 was placed on top of the sensor array 400 so that the border between the two materials laid along the D-D plane, as shown in FIG. 4B. The pad 404 was depressed 0.5 mm and the output of the sensor arrays was measured. The sensor array detected increased forces at the sensor elements compressing the stiffer silicone element 404 compared to the elements compressing the more compliant synthetic fat pad 416 as shown in FIG. 4C.

As a result of these experiments, it has been demonstrated that the sensor arrays of the present disclosure possess a linear response to applied forces and additionally display a high level of spatial acuity. Thus, the sensor arrays of the present disclosure possess the desired properties for an effective surgical tool.

Figure 5A:
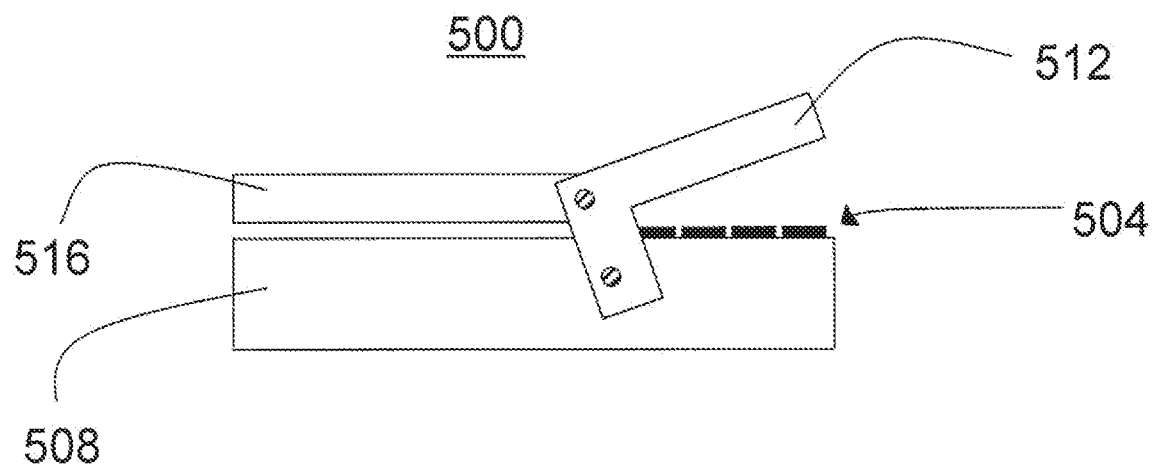
FIG. 5A-5B provides a profile and cross-sectional view of a grasper embodiment of the present disclosure.
Figure 5B:
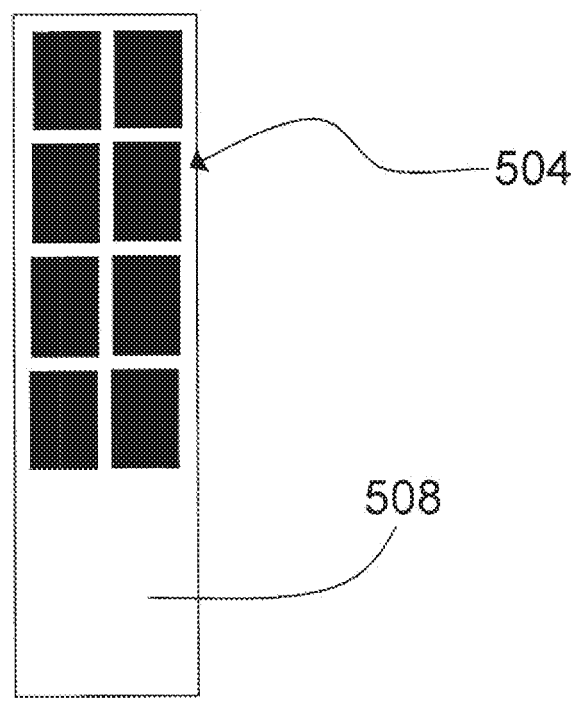

FIG. 5 shows one grasper embodiment 500 of the present disclosure that utilizes sensor arrays as described above. As shown in profile in FIG. 5A, this embodiment is a surgical tool that includes a base 504 in which the sensor array 508 and the accompanying electronic components are found. The top portion includes a grasping jaw 512 that is adapted to open and close onto the sensory array 508 to grasp an object or tissue. This embodiment also includes an arm 516 that is capable of opening and closing the grasping jaw 512 when manipulated by a user during surgery. A face view of the base 508 and sensor array 504 is shown in FIG. 5B. The sensor array 504 is shown as a series of pads in this embodiment. The tool may be fabricated from a wide variety of bio-compatible materials such as stainless steel, plastic, or various composites.

Figure 6:
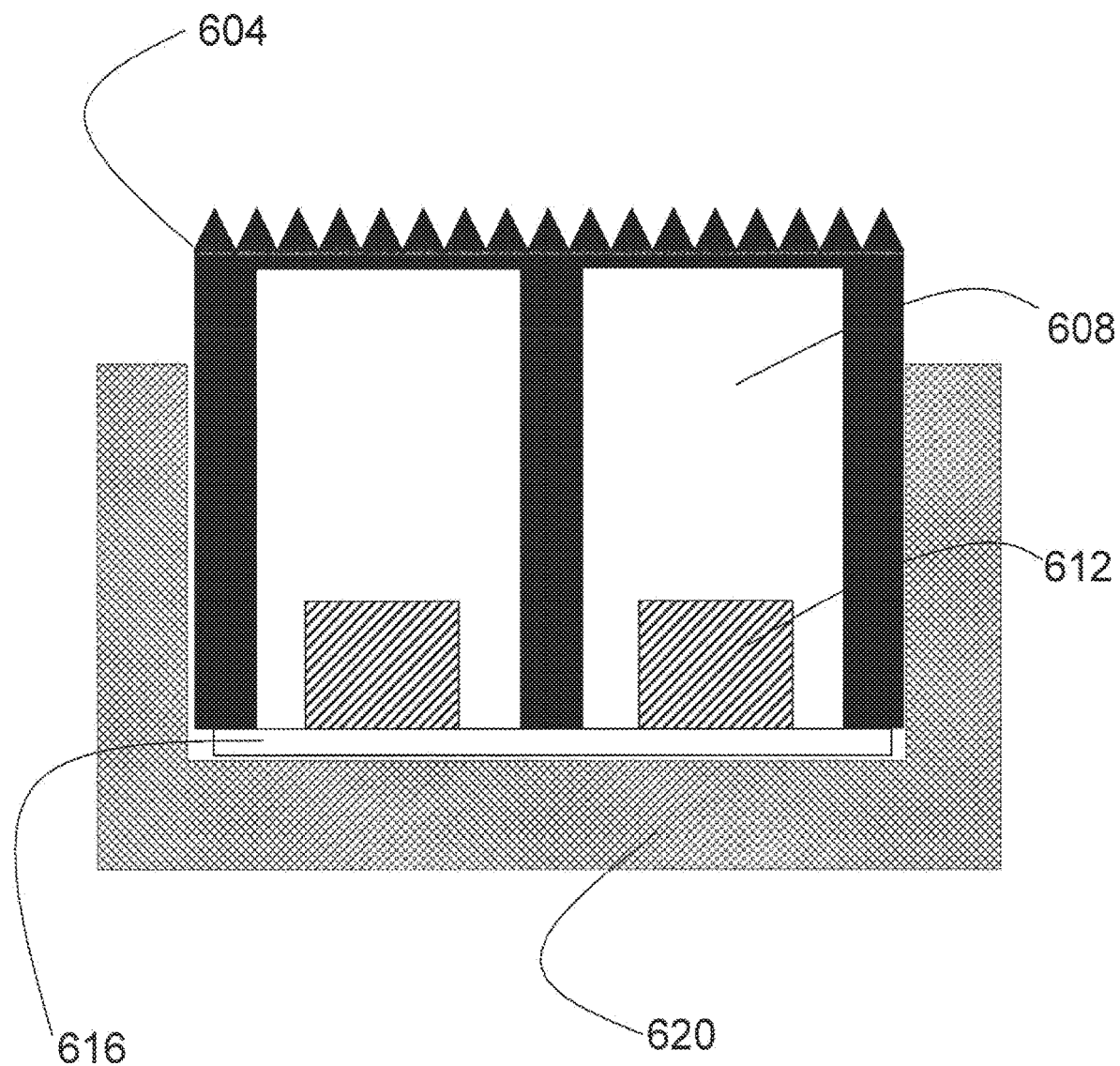
FIG. 6 shows a cross-sectional view of a grasper embodiment of the present disclosure with a face plate.

In other embodiments such as shown in cross-section in FIG. 6, a faceplate 604 may be included in the surgical device and placed on top of the elastomer layer 608 and sensor die 612. As shown in FIG. 6, the sensor die is attached to a printed circuit board 616 and the overall sensor array is housed in a stainless steel or plastic frame 620. The faceplate 604 shown in this embodiment is serrated such as may be employed in grasping and resecting a piece of tissue. The faceplate may, however, possess an appropriate surface for the specific task to be performed by the medical professional utilizing the device. For example, a serrated surface may be preferred for surgical interventions such as grasping or retraction of tissue. Similarly, the faceplate may be modified to be a sharp surface (for scissors or trocar), a flat surface (for simple probing or palpation), or a round surface (such as around the cylindrical shaft of a laparoscopic instrument) for different surgical processes. The micro-pressure sensors included in the present embodiments provide for accurate, repeatable pressure distribution data across the face of the tool, and the faceplate allows for selective and delicate manipulation of tissue.

In some embodiments, measurements obtained through the micro-sensors are sent to an interface to be employed by the user. In one embodiment, the signals can be sent to a graphical display that will inform the user of the pressure being applied to each sensor element. The graphical display may represent the surface of the sensor array and provide information about the forces being sensed at the surface of the surgical tool. The present disclosure may also be implemented, either independently or in combination with a graphical display, as a finger/joystick interface.

Figure 7:
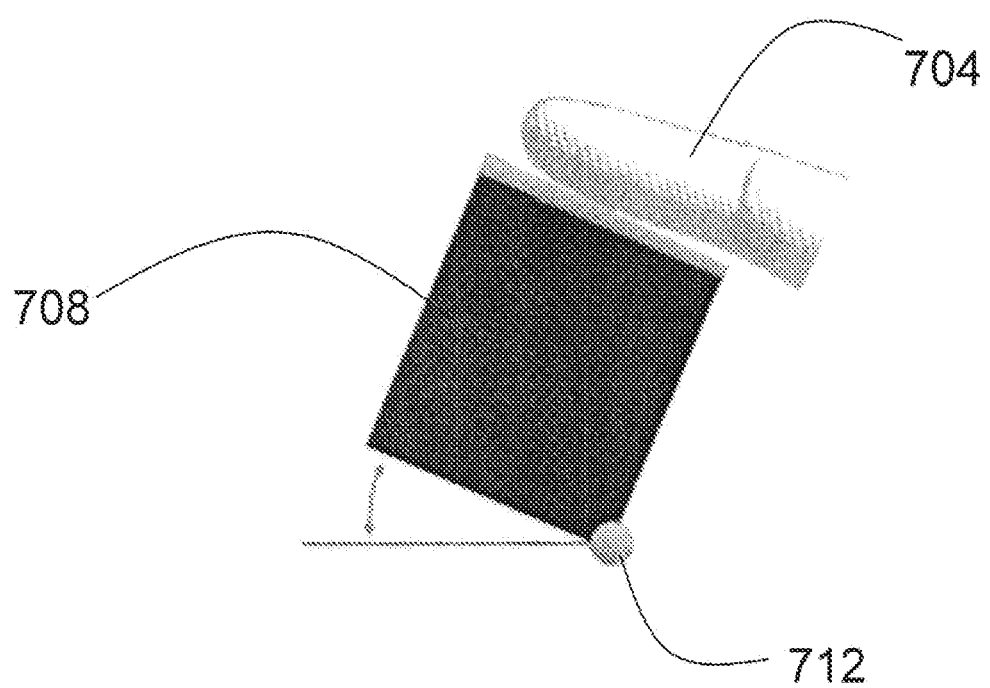
FIG. 7 displays an interface through which a user may utilize the grasper embodiments of the present disclosure.
Figure 8:
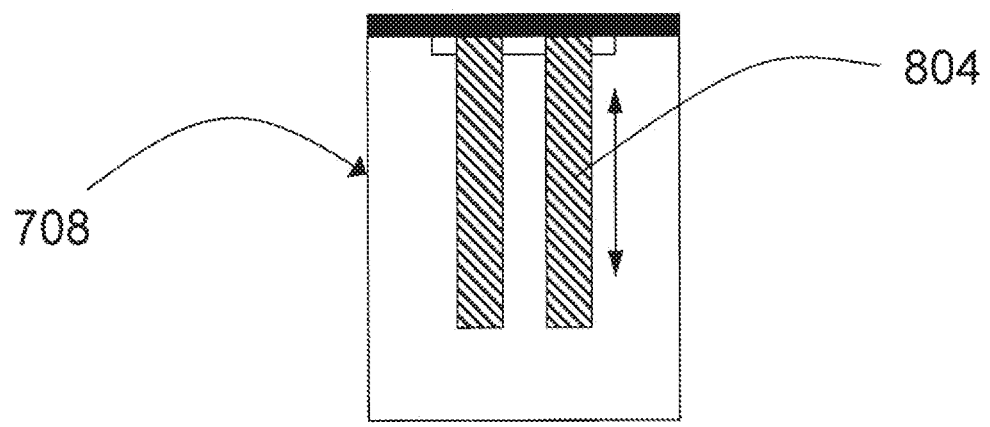
FIG. 8 depicts a cross-section view of an interface through which a user may utilize the grasper embodiments of the present disclosure.

During use, the surgeon may manipulate the grasper joystick by pressing his or her finger 704 against a pad 708, as shown in FIG. 7. The pad 708 may rotate on a pivot 712 and the angle of displacement corresponds to the angle of displacement of the jaws of the tool. When the surgical tool face begins to experience the normal forces of tissue pressing at the jaws, the pivot 712 can lock into place. The pad 708 may also employ spatially mapped pins 804 driven by electrical induction to push on the user's finger proportionally to the pressure distribution measured at the device's jaw, thus providing the user with an accurate haptic representation of the forces measured at the tool face, as shown in FIG. 8. Once the pivot 712 is locked, the solenoid pins 804 may be actuated to press at the user's fingertips with forces proportional to the pressure distribution at the tool jaw (FIG. 4). In some embodiments, the forces at pressure sensors implanted at the tip of the solenoid pins 804 manipulated by the user will correlate with the forces sensed the elastomer at the tool face. The arrangement of solenoid "spring" mechanisms will mimic the compliance properties of the tissue to give the surgeon the feel of the tissue he is grasping.

Figure 9:
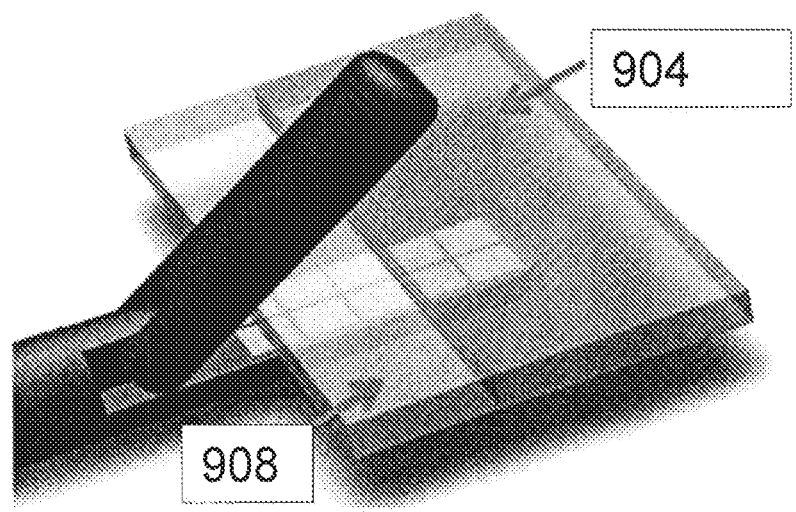
FIG. 9 depicts two physiologic scenarios in which a grasper embodiment of the present disclosure may be used.
Figure 9:
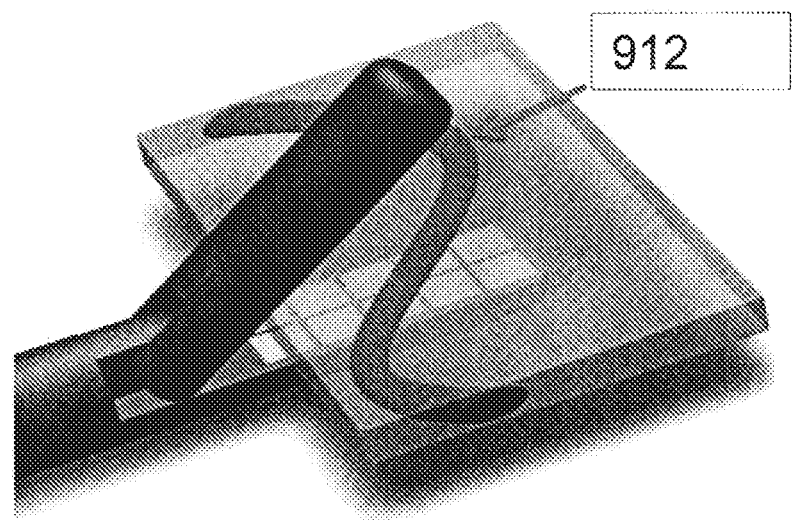

For example, if the tool were being used during an operation to remove neoplastic tissue (FIG. 9), the surgeon would be able to identify the neoplastic tissue 904 as being harder than the surrounding healthy tissue 908 by employing the present disclosure. Alternatively, the interface of the present disclosure may pulse to indicate an underlying artery 912 as also shown in FIG. 9. Furthermore, the present disclosure may also be used to detect structures within fascia or tissue such as underlying non-compliant nerves. In some embodiments, sensor arrays of the present disclosure could be placed onto a probe which could be used to assess firmness of tissue.

Through use of the present disclosure, surgeons and other users will be provided with an accurate haptic sensation of important surgical cues such as the pulsation of an artery; the stiffness of different tissues, and the force with which they are grasping or pulling tissue.

While described in the context of surgical procedures, the present in disclosure may also be employed in a variety of circumstances where remote haptic sensing of forces is desirable. Examples of such scenarios include virtual reality or simulation situations as well. Additionally, the sensor arrays of the present disclosure may also be useful in harsh environment where exposure to humans is detrimental (e.g., corrosive environments) or at locations that are difficult for humans to access.

Nothing in the above description and attached figures is meant to limit the present disclosure to any specific materials, geometry, or orientation of elements. Many modifications are contemplated within the scope of the present disclosure and will be apparent to those skilled in the art. The embodiments disclosed herein were presented by way of example only and should not be used to limit the scope of the disclosure.

We claim:

1. A surgical system for use in robotic surgery on a tissue, comprising;
    a plurality of pressure sensors, wherein the plurality of pressure sensors includes more than four pressure sensors arranged in an array, wherein the plurality of pressure sensors are surrounded by an elastomeric substance;
    a printed circuit board, wherein the plurality of pressure sensors are operably connected to the printed circuit board; and
    a probe device including a faceplate, wherein the probe device includes the plurality of pressure sensors, the elastomeric substance, and the printed circuit board, further wherein the faceplate is disposed adjacent to the elastomeric substance and includes a level surface for probing or palpitation of the tissue;
    wherein the plurality of pressure sensors is adapted to sense forces exerted by the probe device on the tissue; and
    the surgical system further comprising a manipulation interface, wherein the manipulation interface is operably connected to the probe device and is adapted to receive measurements obtained by the plurality of pressure sensors and represent forces exerted by the probe device on the tissue such that a user employing the manipulation interface is able to sense the forces exerted by the probe device on the tissue, and wherein one or more mechanisms of the manipulation interface are driven by electrical induction to provide a haptic sensation including pushing against the user, while the user manipulates the manipulation interface to control the probe device, with forces of the one or more mechanisms pushing against the user proportional to the received measurements of forces exerted by the probe device on the tissue as sensed by the pressure sensors.

2. The surgical system of claim 1, wherein the plurality of pressure sensors are microelectromechanical system-based pressure sensors.

3. The surgical system of claim 1, wherein the elastomeric substance is selected from the group consisting of silicone, non-reactive gel, and non-reactive fluid.

4. The surgical system of claim 1, wherein the probe device includes a bio-compatible metal or plastic.

5. The surgical system of claim 1, wherein each of the plurality of pressure sensors possess a linear response to force.

6. The surgical system of claim 1, wherein the sensor array includes eight pressure sensors.

7. The surgical system of claim 6, wherein the eight pressure sensors are arranged in a 2×4 array.

8. The surgical system of claim 1, wherein the one or more mechanisms of the manipulation interface are further actuated to provide haptic sensation of a pulsation of an artery and/or a stiffness of different tissues based on the forces sensed at the pressure senses.

9. The surgical system of claim 1, wherein the manipulation interface includes a user-engagement member that is manually moveable by a user, wherein movement of the user-engagement member causes corresponding displacement of the faceplate, and further wherein the user-engagement member is configured to lock in place when the plurality of pressure sensors sense a force of the tissue pressing against the faceplate.

10. The surgical system of claim 1, wherein the manipulation interface includes a user-engagement member that is manually moveable by a user, wherein movement of the user-engagement member causes corresponding displacement of a component of the probe device.

11. The surgical system of claim 10, wherein the user-engagement member comprises a joystick interface.

12. The surgical system of claim 1, wherein the manipulation interface comprises a finger interface.

13. A surgical system for use in robotic surgery on a tissue, comprising:
    a plurality of pressure sensors surrounded by an elastomeric substance, wherein the plurality of pressure sensors are arranged in an array;
    a printed circuit board, wherein the plurality of pressure sensors are operably connected to the printed circuit board;
    a probe device including a surface adapted to interface with the tissue, wherein the probe device includes the plurality of pressure sensors, the elastomeric substance, and the printed circuit board, further wherein the surface adapted to interface with the tissue is disposed adjacent to the elastomeric substance and includes a level surface for probing or palpitation of the tissue: and
    a manipulation interface, wherein the manipulation interface is operably connected to the probe device and is adapted to represent a force exerted by the probe device on the tissue such that a user employing the manipulation interface is able to tactilely sense the force exerted by the probe device on the tissue,
    wherein the manipulation interface is configured to pulse to indicate to the user an underlying artery in the tissue.

14. The surgical system of claim 13, wherein the elastomeric substance is selected from the group consisting of silicone, non-reactive gel, and non-reactive fluid.

15. The surgical system of claim 13, wherein the probe device is fabricated of a biocompatible metal or plastic.

16. The surgical system of claim 13, wherein the manipulation interface includes a user-engagement member that is manually moveable by a user, wherein movement of the user-engagement member causes corresponding displacement of the level surface, and further wherein the user-engagement member is configured to lock in place when the plurality of pressure sensors sense a force of the tissue pressing against the level surface.

17. The surgical system of claim 13, wherein each of the plurality of pressure sensors possess a linear response to force.

18. A system for conducting robotic surgery on tissue, comprising:
   a probe device including a faceplate having a level surface for probing or palpitation of a tissue;
   a sensor array disposed within the probe device, the sensor array including a plurality of pressure sensors, wherein the plurality of pressure sensors are arranged in an array and are surrounded by an elastomeric substance, further wherein the plurality of pressure sensors is adapted to sense forces exerted by the probe device on the tissue; and
   a printed circuit board disposed within the probe device, wherein the plurality of pressure sensors is operably connected to the printed circuit board;
   a manipulation interface including a user-engagement member that is manipulatable by a user to control the probe device, wherein the manipulation interface is operably connected to the probe device, receives measurements of a pressure distribution obtained by the plurality of pressure sensors, and provides tactile feedback, via the user-engagement member, to the user, the tactile feedback including a haptic sensation representing the forces exerted by the probe device on the tissue, wherein the manipulation interface provides the tactile feedback to the user by driving spatially mapped mechanisms to push on the user proportionally to the received measurements of the pressure distribution measured by the sensor array.

19. The system of claim 18, wherein the user-engagement member is manually moveable by a user, wherein movement of the user-engagement member causes corresponding displacement of the faceplate, and further wherein the user-engagement member is configured to lock in place when the plurality of pressure sensors sense a force of the tissue pressing against the faceplate.

20. The system of claim 18, wherein the spatially mapped mechanisms comprise a plurality of moveable pins drivable by electrical induction and configured to provide the tactile feedback representing the forces to the user.

21. The system of claim 20, wherein the pins are configured to provide a haptic sensation of surgical cues including a stiffness of different tissues probed or palpitated by the probe device.

22. The system of claim 18, wherein each of the plurality of pressure sensors possesses a linear response to force.

\* \* \* \* \*